United States Patent [19]

Hitzman

[11] 3,975,234

[45] Aug. 17, 1976

[54] MICROBIAL PRODUCTION OF DICARBOXYLIC ACIDS

[75] Inventor: Donald O. Hitzman, Bartlesville, Okla.

[73] Assignee: Phillips Petroleum Company, Bartlesville, Okla.

[22] Filed: July 3, 1975

[21] Appl. No.: 593,141

[52] U.S. Cl. .................................. 195/28 R; 195/49
[51] Int. Cl.² ........................................... C12B 1/00
[58] Field of Search .................. 195/28 R, 49, 36 R, 195/37, 47, 74, 82, 100, 117

[56] References Cited
UNITED STATES PATENTS

| | | | |
|---|---|---|---|
| 3,784,445 | 1/1974 | Dahlstrom et al. | 195/28 R |
| 3,796,630 | 3/1974 | Wegner | 195/28 R |
| 3,822,187 | 7/1974 | Chaffaut et al. | 195/28 R |
| 3,843,466 | 10/1974 | Akabori et al. | 195/28 R |

*Primary Examiner*—A. Louis Monacell
*Assistant Examiner*—R. B. Penland

[57] ABSTRACT

Dicarboxylic acids are produced by enzymatic fermentation of the respective hydrocarbon and/or a corresponding alcohol utilizing under nongrowth conditions the mutant strains of microorganism *Torulopsis bombicola* which has been grown on hydrocarbon-free media, namely, on carbohydrates, e.g., sugar.

8 Claims, No Drawings

MICROBIAL PRODUCTION OF DICARBOXYLIC ACIDS

The present invention relates to the production of dicarboxylic acids. More specifically, the present invention relates to the fermentation of n-alkanes or the corresponding alcohol to produce dicarboxylic acids utilizing the microorganism *Torulopsis bombicola*.

BACKGROUND OF THE INVENTION

It is well known in the art that mutant strains of *Torulopsis bombicola* effectively convert n-alkanes into the corresponding dicarboxylic acids. This process is described in U.S. Pat. No. 3,796,630, which issued on Mar. 12, 1974, to Eugene H. Wegner.

This process has proven to be quite successful. However, the conversion time for the production of the dicarboxylic acid was high. It would, therefore, be desirable to produce the dicarboxylic acid at a higher speed.

THE INVENTION

It is one object of this invention to provide a process for the production of dicarboxylic acids.

Another object of this invention is to provide a process for the microbial production of dicarboxylic acids employing the microorganism *Torulopsis bombicola*.

Still a further object of this invention is to provide a process for the improved production of the dicarboxylic acids by microbial fermentation of n-alkanes or the corresponding alcohol.

These and other objects, advantages, embodiments and details of the invention will become apparent to those skilled in the art from the following description of the invention and the appended claims.

In accordance with this invention, I have found that mutant strains of *Torulopsis bombicola*, having been grown on nonhydrocarbon media, converts n-alkanes and the corresponding alcohols into dicarboxylic acids under nongrowth conditions in a relatively short period of time.

More specifically, there is provided in accordance with this invention a process for the production of dicarboxylic acids which comprises (A) growing the microorganisms of the mutant strains of *Torulopsis bombicola* on a hydrocarbon-free growth medium containing a carbohydrate source, (B) separating at least a portion of the microorganisms from the growth medium, (C) introducing at least a portion of these microorganisms into a converting medium under nongrowth conditions, (D) contacting these microorganisms in this nongrowth converting medium with n-alkane or the corresponding alcohol such as to partially convert this n-alkane or alcohol into the corresponding dicarboxylic acid having the same number of carbon atoms as the n-alkane or the corresponding alcohol, and (E) recovering the dicarboxylic acid from the converting medium.

The parent culture of *Torulopsis bombicola*, $\eta_{sp}$, PRL 319-67, is obtainable from Prairie Regional Laboratory, National Research Council of Canada, Saskatoon, Saskatchewan. The yeast mutant employed in the present invention is produced in accordance with the following preferred procedure.

A 0.5 ml sample of a 3-day culture of *Torulopsis bombicola* grown on an after-defined sucrose-containing nutrient is added to 100 ml of an after-defined glucose-containing nutrient and the mixture is agitated for a period of about five hours. Thereafter, 5 ml of a 300 milligrams per 100 ml solution of N-methyl-N-nitroso-N'-nitroguanidine is added to the culture. Agitation is continued for about one-fourth hour and a 1 milliliter sample is removed and plated on plates at a $10^5$ dilution.

After 6 days' incubation at 25°C., the plates, averaging 26 colonies per plate, are replicated on nonglucose-based media containing 0.2 weight percent methyl laurate and on the glucose-containing nutrient.

After 6 days' incubation at 25°C. colonies which develop on the glucose-containing nutrient but not on the methyl laurate-containing media are selected and tested to determine if they produce long-chain dicarboxylic acids from n-paraffins.

The glucose-containing nutrient employed in the above-described procedure for producing the mutant was of the following composition per liter of aqueous solution.

| Component: | Grams per Liter |
|---|---|
| Commercial yeast extract | 3 |
| Malt extract | 3 |
| Peptone | 5 |
| Glucose | 10 |

The time for the conversion of $C_6$ to $C_{22}$, preferably $C_{16}$ to $C_{22}$, n-alkanes or alcohols into the corresponding dicarboxylic acids according to this invention is about 20 to about 50 hours, although the microorganism has never before "seen" any hydrocarbons or alcohol. The preferred reaction or converting time is about 30 hours.

The temperature of the conversion is usually in the range of about 15° to about 45°C. Preferably, this temperature is between about 20° and about 30°C.

In accordance with one presently preferred embodiment of this invention, the microorganism is grown on a growth medium comprising at least one carbohydrate and yeast extract or other nitrogen source such as peptones, ammonia, urea or ammonium nitrate. The preferred yeast extract constitutes a nitrogen source necessary for the growth of the organism. Good results are achieved by including into the growth medium a mineral solution, as well as small amounts of $KH_2PO_4$ and $MgSO_4$. The growth medium preferably contains these ingredients per liter of water in the following ranges:

| Composition of the Growth Medium Component | | |
|---|---|---|
| Carbohydrate | 20–50 | g/l |
| Yeast extract | 2–10 | g/l |
| $KH_2PO_4$ | 0.5–2.0 | g/l |
| $MgSO_4$ | 1.0–5.0 | g/l |
| Trace mineral solution | 0.5–5 | ml/l |

Throughout this specification g/l is used as an abbreviation for grams per liter and ml/l as an abbreviation for milliliters per liter.

Whereas a wide variety of carbohydrates can be used to grow the microorganism, it is presently preferred to grow them in a growth medium containing at least one carbohydrate selected from the group consisting of sucrose, glycerol, molasses, glucose, and starch.

The nongrowth converting medium can comprise various ingredients, the important limitation being, however, that the nongrowth converting medium does not contain a nitrogen source such as yeast extracts, peptone, or other nitrogen sources as ammonia or derivatives thereof such as urea or ammonium nitrate which can be utilized by the organism for cell reproduction, i.e., growth. In other words, the nongrowth converting medium lacks at least one essential growth ingredient.

The presently preferred nongrowth converting medium is an aqueous solution comprising essentially the same ingredients as the growth medium with the important exception, however, that at least one essential growth ingredient is missing, e.g., no nitrogen source is present. Thus, in particular, no yeast extract is present in the converting medium. The preferred converting medium comprises a carbohydrate, $KH_2PO_4$, $MgSO_4$ and a mineral solution. The ranges for the quantities of these ingredients are the same as given above for the corresponding ingredients in the growth medium table.

While any carbohydrate can be used, the preferred carbohydrates to be included in the nongrowth converting medium is one selected from the group consisting of sucrose, glycerol, starch or mixtures of these. The nongrowth converting medium may also contain a small quantity of an alkali metal citrate, particularly sodium citrate, in order to reduce the production of the monoacids.

The microorganisms are separated from the growth medium by standard sampling techniques. The diacid is recovered by standard technologies well known in the art such as solvent extraction and fractional distillation. At the end of the process the microorganisms, having produced the diacids, are no longer viable. These microorganisms, in accordance with a preferred embodiment of this invention, are recovered and used as a protein source, e.g., in animal feed materials.

The invention will be more fully understood from the following examples, which are intended to illustrate preferred embodiments of this invention but not to limit the scope of protection.

EXAMPLE I

Two mutant cultures of *Torulopsis bombicola* were used as the test organisms. Both these organisms, called 11-11 and 82-3f3, were grown as described above. Both are mutants of the parent *Torulopsis bombicola* which have been selected for their ability to rapidly convert hydrocarbons to diacids. The cultures were grown on media with the following composition:

| Media Composition | |
|---|---|
| Component | |
| Carbohydrate* | 40 g/l |
| Yeast extract | 5 g/l |
| $KH_2PO_4$ | 1 g/l |
| $MgSO_4$ | 3 g/l |
| Trace mineral solution | 1 ml/l |

*Carbohydrate was varied in composition asshown in the tables.

The trace mineral solution mentioned above had the following composition:

| Trace Mineral Solution | |
|---|---|
| Component | |
| $CuSO_4.5H_2O$ | 0.06 g/l |

| -continued | |
|---|---|
| Trace Mineral Solution | |
| Component | |
| KI | 0.08 g/l |
| $MnSO_4.H_2O$ | 0.3 g/l |
| $Na_2MoO_4.2H_2$ | 0.2 g/l |
| $H_3BO_3$ | 0.02 g/l |
| $ZnSO_4.7H_2O$ | 2.0 g/l |
| $FeCl_3.6H_2O$ | 4.8 g/l |
| $H_2SO_4$ (conc.) | 2 ml/l |

The cultures were allowed to grow for 48 hours with an air flow of about 0.1 to 0.2 volume of air per volume of medium per minute, agitating the medium at 600 to 800 rpm. No pH control was required.

After the growth, the fermentor effluent was harvested and centrifugated for 10 minutes at 2,500 rpm. The centrifuge was operated with 6 cups containing 300 grams each of the fermentor effluent. The supernatant liquid was decanted and discarded and the packed cells were resuspended in a nongrowth medium having the following composition:

| Nongrowth Converting Medium | |
|---|---|
| Component | |
| Carbohydrate* | 10 g/l |
| $KH_2PO_4$ | 1 g/l |
| $MgSO_4$ | 3 g/l |
| Trace mineral solution | 1 ml/l |

*Carbohydrate was varied in composition as shown in the tables.

The cells were concentrated by a factor of 6 in comparison to the growth medium in order to prepare a heavier cell suspension. Thus, there were six times as many cells in a volume unit of conversion medium than there were in the same volume of growth medium when it was harvested.

To the thus-prepared nongrowth medium containing the cells or the mutant strains of *Torulopsis bomblcola*, one weight percent of $C_{16}$ n-paraffin was added. 100 cc samples were filled into 2-liter fluted flasks. These flasks were agitated on a rotary shaker at room temperature for a period of 24 to 30 hours. 50 gram aliquots were removed at intervals and analyzed for diacid concentration. These aliquots were extracted with 50 cubic centimeters of ethyl ether in order to prepare them for a gas-liquid chromatography test. The samples were shaken for 30 seconds, and a 10 cubic centimeter sample of the ether layer was removed, dried, and 2.5 cc of boron trifluoride in methanol was added. The samples were then warmed in hot water for 15 minutes, cooled, and 2.5 cc of deionized water were added, followed by 1.5 cc of hexane. This hexane extract was analyzed by temperature-programmed gas-liquid chromatograph (GLC) with the peak heights being measured. A quantitative comparison could be made of the ratio of peak heights of the produced acids to the residual hydrocarbon in the sample. These peak height ratios shown in the following table indicate the relative concentrations of the respective constituents in the liquid introduced into the gas-liquid chromatographic analyzer. Since different batches were prepared in the various fermentations, the ratios are comparative between samples in one series but not between different series.

The results of these experiments and tests are shown in the following tables:

TABLE I

| Growth Conditions and carbohydrate content in converting medium | Ratio of Peak Heights of Produced Acids to Residual Hydrocarbons by GLC | | | | |
|---|---|---|---|---|---|
| | $C_{12}$ diacid | $C_{16}$ mono-acid | $C_{14}$ diacid | $C_{18}$ mono-acid | $C_{16}$ diacid |
| A) Culture 11-11 | | | | | |
| I) Grown on 10 g/l sucrose + 30 g/l glycerol medium The nongrowth converting medium contained | | | | | |
| 1. 10 g/l sucrose | | 4.9 | | .11 | 3.96 |
| 2. 10 g/l glycerol | | 7.0 | | .15 | 3.63 |
| 3. 10 g/l starch | | 1.19 | | .17 | 1.15 |
| II) Grown on 30 g/l sucrose + 10 g/l glucose medium The nongrowth converting medium contained | | | | | |
| 4. 10 g/l sucrose | | 2.91 | | .3 | 1.46 |
| 5. 10 g/l glycerol | | 1.28 | | .06 | .75 |
| 6. 10 g/l starch | | .01 | | .01 | .6 |
| III) Grown on 30 g/l sucrose + 10 g/l starch medium The nongrowth converting medium contained | | | | | |
| 7. 10 g/l sucrose | | 4.79 | | .17 | 1.93 |
| 8. 10 g/l glycerol | | 3.02 | | .05 | 2.69 |
| 9. 10 g/l starch | | .13 | | .07 | .54 |
| B) Culture 82-3f3 | | | | | |
| I) Grown on 10 g/l sucrose + 30 g/l glycerol medium The nongrowth converting medium contained | | | | | |
| 1. 10 g/l sucrose | | .79 | .34 | .04 | 1.75 |
| 2. 10 g/l glycerol | .29 | 1.60 | .79 | .08 | 5.5 |
| 3. 10 g/l starch | .18 | .18 | .53 | .03 | 2.6 |
| II) Grown on 30 g/l sucrose + 10 g/l glucose medium The nongrowth converting medium contained | | | | | |
| 4. 10 g/l sucrose | .07 | .68 | .39 | .09 | 1.92 |
| 5. 10 g/l glycerol | | .14 | | | 1.33 |
| 6. 10 g/l starch | | .14 | | .01 | .81 |
| III) Grown on 30 g/l sucrose + 10 g/l starch medium The nongrowth converting medium contained | | | | | |
| 7. 10 g/l sucrose | .04 | .86 | .48 | .12 | 3.06 |
| 8. 10 g/l glycerol | .06 | .3 | .34 | .1 | 2.08 |
| 9. 10 g/l starch | .01 | .05 | .01 | | .45 |

As can be seen from the table, the growth media which produced the optimum results differ somewhat for the different cultures. In all the instances, however, the best results as far as the yield of the diacid is concerned were obtained by including either sucrose or glycerol in the converting medium. The use of starch as the carbohydrate in the converting medium considerably reduced the yield of the $C_{16}$ diacid. However, the ratio of $C_{16}$ diacid and $C_{16}$ monoacid is improved by the use of starch as the carbohydrate in the converting medium.

Furthermore, the diacid formation under nongrowth conditions was achieved in 24 to 30 hours. Under growth conditions the fermentation time is around 140 hours. In addition, the microorganisms having carried out the reaction are a useful product which can be added as a protein source to animal feed, since these microorganisms are no longer capable of reproduction or growth.

EXAMPLE II

The procedure of Example I was essentially repeated, however, instead of growing the cultures on media composed of two different carbohydrate sources, the cultures were grown on a medium which instead of 40 g/l carbohydrates contained 30 g/l of sucrose. The cells were exposed under nongrowth conditions to 10 g/l of $C_{16}$ n-paraffin. Several separate runs were made wherein different carbohydrates were incorporated into the nongrowth converting medium as shown in the following table. The results of these runs are also shown in the following table. In case of the culture 11-11, Run 2, some $C_{18}$ diacid was produced. In case of the culture 82-3f3, Runs 1 and 4, some $C_{12}$ diacid and some $C_{14}$ diacid was produced in both cases.

TABLE II

| | Ratio of Peak Heights of Product Acid to Residual Hydrocarbons by GLC | | |
|---|---|---|---|
| A) Culture 11-11 | $C_{16}$ monoacid | $C_{18}$ monoacid | $C_{16}$ diacid |
| 1. 10 g/l sucrose | 5.35 | .41 | 1.86 |
| 2. 10 g/l lactose | .4 | .49 | .37 |
| 3. 10 g/l maltose | .28 | .43 | .31 |
| 4. 10 g/l galactose | .45 | .27 | .4 |
| 5. 10 g/l glycerol | 1.24 | .32 | 2.51 |
| 6. 10 g/l starch | .26 | .37 | .30 |
| B) Culture 82-3f3 | | | |
| 1. 10 g/l sucrose | .55 | .21 | 2.92 |
| 2. 10 g/l lactose | .3 | .02 | .74 |
| 3. 10 g/l maltose | .24 | .4 | .86 |
| 4. 10 g/l galactose | .04 | .09 | .5 |
| 5. 10 g/l glycerol | .21 | .36 | 1.31 |
| 6. 10 g/l starch | .04 | .37 | .95 |

The results of the above table show that again sucrose and glycerol are the most desirable carbohydrate sources for the nongrowth converting medium. As in the first example and in this example, too, sucrose gave the optimum $C_{16}$ diacid production for the culture 82-

3f3 whereas glycerol gave the best results for the culture 11-11.

EXAMPLE III

Example I was repeated with the following changes: Instead of the mixed growth medium, the culture 11-11 in this example was grown on a 40 g/l sucrose medium. The cells were exposed in nongrowth conditions to the medium described with 10 g/l $C_{16}$ n-paraffin. In addition to 10 g/l carbohydrate as specified in the following table, the nongrowth converting medium for some runs also contained sodium citrate and/or sodium acetate in the quantities specified in the following table.

TABLE III

| | | Ratio of Peak Heights of Product Acid to Residual Hydrocarbons by GLC | | |
|---|---|---|---|---|
| The nongrowth converting medium contained | | $C_{16}$ monoacid | $C_{18}$ monoacid | $C_{16}$ diacid |
| 1. | 10 g/l sucrose | 8.95 | .28 | 3.73 |
| 2. | 10 g/l sucrose + 2 g/l Na citrate | .97 | .09 | 2.19 |
| 3. | 10 g/l sucrose + 2 g/l Na acetate | .65 | .03 | .72 |
| 4. | 10 g/l sucrose + 2 g/l Na citrate + 2 g/l Na acetate | .24 | .03 | .80 |
| 5. | 10 g/l glycerol | 6.02 | .09 | 3.25 |
| 6. | 10 g/l glycerol + 2 g/l Na citrate | 1.33 | .02 | 1.88 |
| 7. | 10 g/l glycerol + 2 g/l Na acetate | 1.07 | .01 | 1.79 |
| 8. | 2 g/l Na citrate | .40 | .15 | .74 |
| 9. | 2 g/l Na acetate | .13 | .04 | .34 |

As can be seen from the above table, the addition of sodium citrate or acetate increased the ratio of the $C_{16}$ diacid to $C_{16}$ monoacid production. However, the yield was reduced.

EXAMPLE IV

Example I was essentially repeated. However, the culture 11-11 was grown on media containing two carbohydrate sources as specified in the following table. In addition, the cells were exposed under nongrowth conditions to 10 g/l of $C_{16}$ n-paraffin. The nongrowth converting medium also contained various carbohydrate sources and in some runs sodium citrate. The results are shown in the following table.

TABLE IV

| | Ratio of Peak Heights of Product Acid to Residual Hydrocarbons by GLC | | |
|---|---|---|---|
| | $C_{16}$ monoacid | $C_{18}$ monoacid | $C_{16}$ diacid |
| A) Grown on 10 g/l sucrose 30 g/l glycerol | | | |
| The nongrowth converting medium contained/liters | | | |
| 1. 10 g/l sucrose | 4.1 | .04 | 3.0 |
| 2. 10 g/l sucrose + 2 g/l Na citrate | 1.5 | .03 | 2.2 |
| 3. 10 g/l glycerol | 6.2 | .12 | 4.1 |
| 4. 10 g/l glycerol + 2 g/l Na citrate | 4.7 | .1 | 3.2 |
| B) Grown on 20 g/l sucrose 20 g/l glycerol | | | |
| The nongrowth converting medium contained/liters | | | |
| 5. 10 g/l sucrose | 6.1 | .14 | 3.4 |
| 6. 10 g/l sucrose + 2 g/l Na citrate | 2.3 | .03 | 2.1 |
| 7. 10 g/l glycerol | 5.39 | .13 | 2.61 |
| B. 10 g/l glycerol + 2 g/l Na citrate | 3.13 | .07 | 3.13 |
| C) Grown on 30 g/l sucrose 10 g/l glycerol | | | |
| The nongrowth converting medium contained/liters | | | |

TABLE IV-continued

| | Ratio of Peak Heights of Product Acid to Residual Hydrocarbons by GLC | | |
|---|---|---|---|
| | $C_{16}$ monoacid | $C_{18}$ monoacid | $C_{16}$ diacid |
| 9. 10 g/l sucrose | 8.28 | .19 | 6.04 |
| 10. 10 g/l sucrose + 2 g/l Na citrate | 1.02 | .02 | 1.32 |
| 11. 10 g/l glycerol | 3.48 | .1 | 2.13 |
| 12. 10 g/l glycerol + 2 g/l Na citrate | 2.90 | .09 | 2.01 |

This example shows that the addition of sodium citrate increases the selectivity to the diacid. The ratio of monoacid to diacid produced is reduced by the addition of the sodium citrate.

EXAMPLE V

The culture 11-11 was grown on a 40 g/l sucrose medium followed by an exposure of the cells in a nongrowth medium to 10 g/l $C_{16}$ n-paraffin. The operation was carried out as described in Example I. In addition, the non-growth medium contained varying amounts of sodium citrate. The results in peak heights of the gas-liquid chromatograph are shown in the following table.

TABLE V

| | Ratio of Peak Heights of Product Acid to Residual Hydrocarbons by GLC | | |
|---|---|---|---|
| Nongrowth medium contained | $C_{16}$ monoacid | $C_{18}$ monoacid | $C_{16}$ diacid |
| 1. 10 g/l sucrose | 9.0 | .24 | 4.19 |
| 2. 10 g/l sucrose + 1 g/l Na citrate | 2.42 | .09 | 1.82 |
| 3. 10 g/l sucrose + 2 g/l Na citrate | 1.4 | .04 | 1.18 |
| 4. 10 g/l sucrose + 5 g/l Na citrate | 1.25 | .15 | 1.61 |
| 5. 10 g/l glycerol + 1 g/l Na citrate | 2.34 | .05 | 2.5 |
| 6. 10 g/l glycerol + 2 g/l Na citrate | 1.89 | .02 | 1.82 |
| 7. 10 g/l glycerol + 5 g/l Na citrate | 1.60 | .07 | 1.7 |
| 8. g/l starch + 2 g/l Na citrate | .37 | .10 | .57 |
| 9. 10 g/l starch + 2 g/l Na acetate | .03 | .01 | .43 |

From the above shown data it can be seen that whereas the presence of a small quantity of sodium citrate has a considerable effect on the ratio of the diacid to the monoacid produced, a further increase of the quantity of the sodium citrate further improves this result but does so at a reduced rate of production of the desired acids. Sodium acetate further reduces the overall yield while improving selectivity to the diacid.

EXAMPLE VI

Since it is assumed that cetyl alcohol is an intermediate product in the enzymatic conversion of the $C_{16}$ n-paraffin to the corresponding diacid, the following runs were carried out utilizing cetyl alcohol together with $C_{16}$ n-paraffin in the nongrowth medium. The culture utilized was the microorganism 11-11 grown on a 40 g/l sucrose medium. The operation was the same as in Example I. The results obtained are shown in the following Table VI.

Two runs were carried out in which no $C_{16}$ n-paraffin was used in the nongrowth medium, but only cetyl alcohol was utilized. The ratios given in the following table are calculated on the basis of the remaining cetyl alcohol.

TABLE VI

|  | $C_{16}$ monoacid | $C_{18}$ monoacid | $C_{16}$ diacid |
|---|---|---|---|
| A) The nongrowth samples contained 10 g/l $C_{16}$ n-paraffin and, per liter | | | |
| 1. 10 g/l sucrose | .87 | .22 | .15 |
| 2. 10 g/l sucrose + 10 g/l cetyl alcohol | 3.8 | .51 | .52 |
| 3. 10 g/l glycerol | .32 | .15 | .26 |
| 4. 10 g/l glycerol + 10 g/l cetyl alcohol | 5.0 | .62 | .42 |
| B) The nongrowth samples contained no $C_{16}$ n-paraffin; they contained: | | | |
| 5. 10 g/l sucrose + 2 g/l cetyl alcohol | 6.0 | 2.0 | 1.6 |
| 6. 10 g/l glycerol + 10 g/l cetyl alcohol | 1.0 | .07 | .3 |

As can be seen from the table, cetyl alcohol is also converted into the diacid by enzymatic fermentation with the microorganizm specified. The addition of cetyl alcohol to the nongrowth medium in addition to the $C_{16}$ n-paraffin caused a higher yield of the overall product, both mono- and diacids. However, the ratio of the mono- to the diacid was also increased so that less of the more desirable diacid was produced.

Reasonable variations and modifications which will be apparent to those skilled in the art can be made in this invention without departing from the spirit and scope thereof.

I claim:

1. A process to produce dicarboxylic acids comprising utilizing a microorganism of the mutant strains of *Torulopsis bombicola*, η sp; PRL 319-67, Prairie Regional Laboratory, National Research Council of Canada, having been grown on a hydrocarbon-free growth medium containing at least one carbohydrate source, contacting the so grown microorganism under non-growth conditions in a non-growth converting medium being free of a nitrogen source for the microorganism with a compound selected from the group consisting of n-alkanes, n-alkyl alcohols and mixtures thereof such as to at least partially convert said compound into the corresponding dicarboxylic acid having the same number of carbon atoms as said compounds, and recovering said dicarboxylic acid from said converting medium.

2. A process in accordance with claim 1 wherein said n-alkane and said n-alkyl alcohol have from about 16 to about 22 carbon atoms.

3. A process in accordance with claim 1 wherein said rowth medium contains a nitrogen source selected from the group consisting of yeast extracts, peptones, ammonia, ammonium nitrate, urea, proteins, and a carbohydrate source selected from the group consisting of sucrose, glycerol, and starch.

4. A process in accordance with claim 1 wherein said non-growth converting medium contains a carbohydrate source selected from the group consisting of sucrose, glycerol and starch.

5. A process in accordance with claim 1 wherein said growth medium contains yeast extract, $KH_2PO_4$, $MgSO_4$ and a trace mineral solution.

6. A process in accordance with claim 1 wherein said nongrowth converting medium contains a monoacid suppressing agent selected from the group consisting of alkali metal citrates and alkali metal acetates.

7. A process in accordance with claim 6 wherein the nongrowth converting medium contains sodium citrate.

8. A process in accordance with claim 1 wherein a compound selected from the group consisting of n-alkanes and n-alkyl alcohols both having from 16 to 18 carbon atoms and mixtures thereof is used and the microbial conversion is carried out at a temperature of about 15° to about 40°C. for a period of time of about 20 to about 50 hours.

* * * * *